United States Patent [19]
Bonutti

[11] Patent Number: 6,007,567
[45] Date of Patent: *Dec. 28, 1999

[54] SUTURE ANCHOR

[76] Inventor: Peter M. Bonutti, 1303 W. Evergreen Plaza, Effingham, Ill. 62401

[ * ] Notice: This patent is subject to a terminal disclaimer.

[21] Appl. No.: 09/259,759

[22] Filed: Mar. 1, 1999

Related U.S. Application Data

[60] Continuation of application No. 08/964,167, Nov. 4, 1997, which is a division of application No. 08/699,553, Aug. 19, 1996, Pat. No. 5,718,717.

[51] Int. Cl.⁶ .................................................. A61B 17/04
[52] U.S. Cl. ............................................................ 606/232
[58] Field of Search ............................ 606/232, 75, 213, 606/214, 215

[56] References Cited

U.S. PATENT DOCUMENTS

| | | |
|---|---|---|
| 4,235,238 | 11/1980 | Ogiu et al. . |
| 4,448,194 | 5/1984 | DiGiovanni et al. . |
| 4,741,330 | 5/1988 | Hayhurst .................................. 606/232 |
| 4,890,612 | 1/1990 | Kensey . |
| 5,002,550 | 3/1991 | Li . |
| 5,021,059 | 6/1991 | Kensey et al. . |
| 5,041,129 | 8/1991 | Hayhurst et al. . |
| 5,061,274 | 10/1991 | Kensey . |
| 5,100,417 | 3/1992 | Cerier et al. . |
| 5,354,298 | 10/1994 | Lee et al. . |
| 5,370,660 | 12/1994 | Weinstein et al. . |
| 5,403,348 | 4/1995 | Bonutti .................................. 606/232 |
| 5,405,359 | 4/1995 | Pierce . |
| 5,464,426 | 11/1995 | Bonutti . |
| 5,522,844 | 6/1996 | Johnson . |
| 5,545,178 | 8/1996 | Kensey et al. .......................... 606/232 |
| 5,549,631 | 8/1996 | Bonutti .................................. 606/232 |
| 5,718,717 | 2/1998 | Bonutti .................................. 606/232 |

*Primary Examiner*—Gary Jackson
*Attorney, Agent, or Firm*—Tarolli, Sundheim, Covell, Tummino & Szabo LLP

[57] ABSTRACT

A suture anchor is formed of a material which absorbs body liquid when exposed to body liquid. The anchor may be at least partially formed of a material having a strong affinity for body liquids. This enables the anchor to absorb body liquid and expand upon being inserted into a patient's body. At least one embodiment of the suture anchor has portions formed of a relatively hard material which does not absorb body liquids and is pressed against body tissue by the material which absorbs body liquid to mechanically interlock the suture anchor and the body tissue. The anchor may be at least partially formed of a cellular material. The cells expand to absorb body liquid. At least one embodiment of the anchor has a pointed leading end portion to form an opening in an imperforate surface on body tissue. The configuration of the anchor may be changed by tensioning the suture while the anchor is disposed in body tissue.

12 Claims, 5 Drawing Sheets

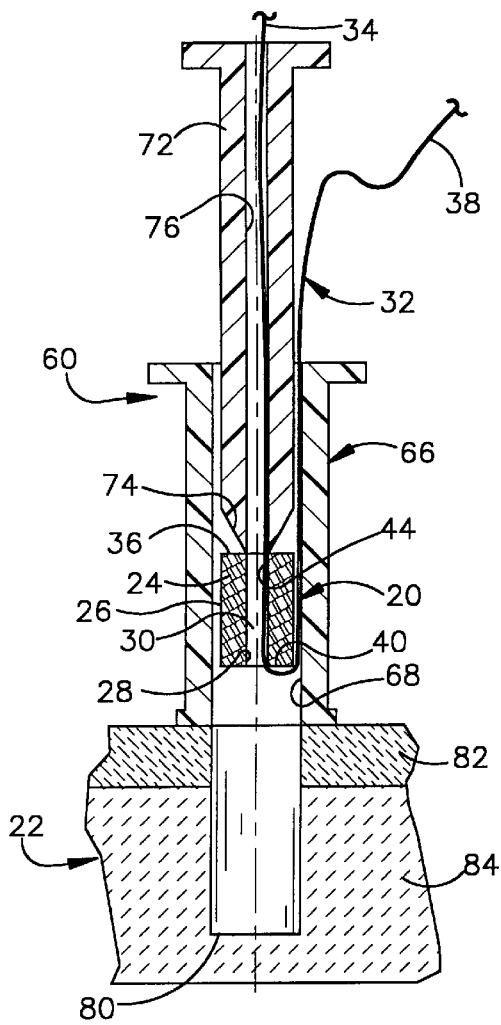
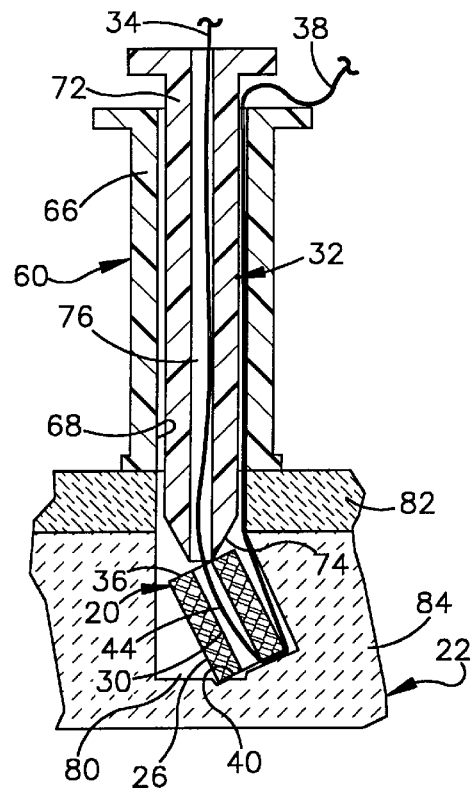
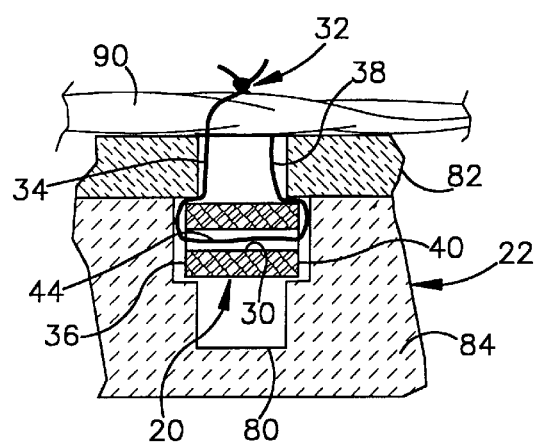
Fig.1
Fig.2
Fig.3

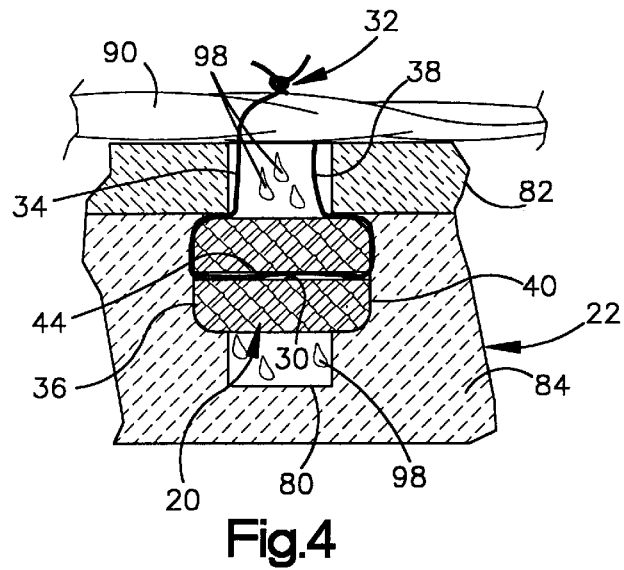
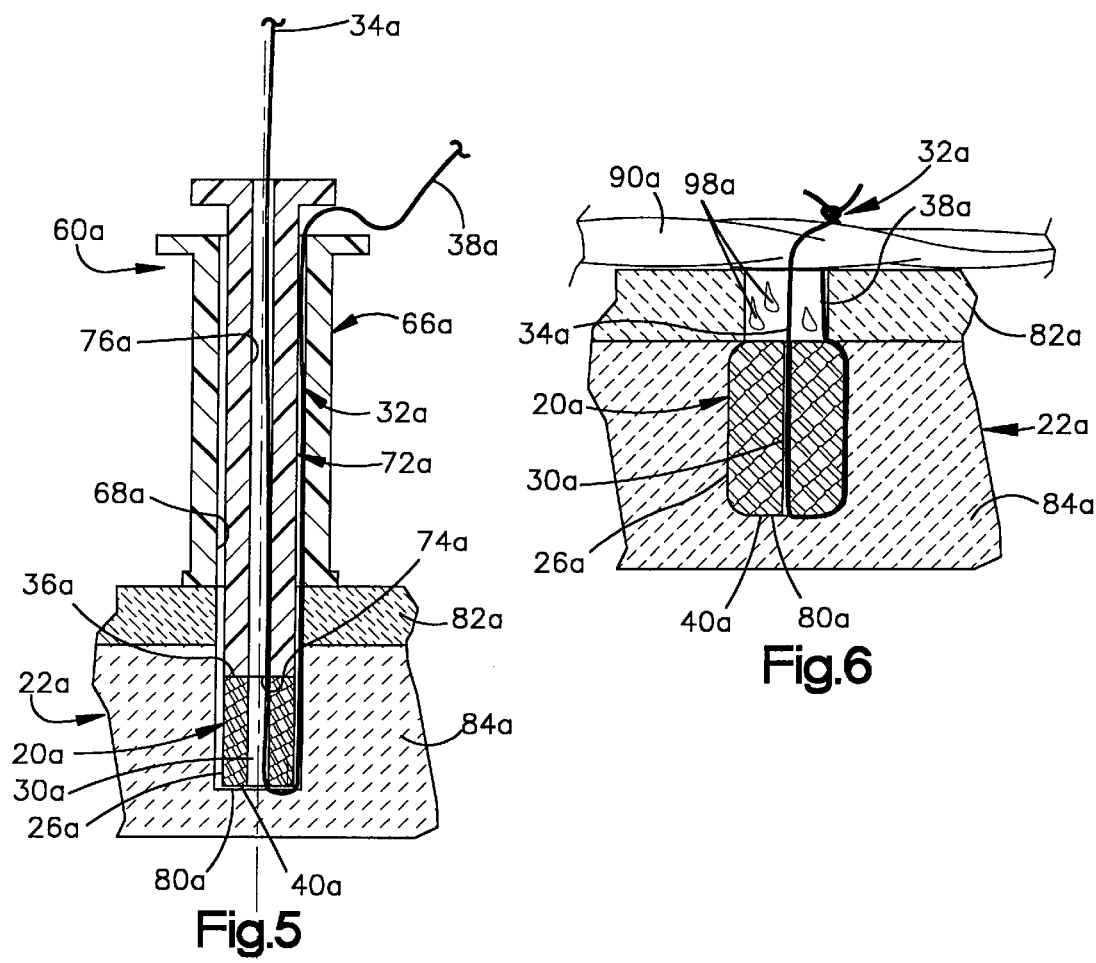

SUTURE ANCHOR

This is a continuation of copending application Ser. No. 08/964,167 filed Nov. 4, 1997. The aforementioned application Ser. No. 08/964,167 is itself a divisional of application Ser. No. 08/699,553 filed Aug. 19, 1996, now U.S. Pat. No. 5,718,717. The benefit of the earlier filing dates of the aforementioned applications is hereby claimed.

BACKGROUND OF THE INVENTION

The present invention relates to a new and improved suture anchor and more specifically to a suture anchor which is capable of expanding in a patient's body to enable the anchor to withstand relatively large pull-out forces.

Anchors are commonly utilized to retain sutures in a patient's body. The anchors have previously been formed of metal, such as stainless steel or titanium. In addition, anchors have been formed of biodegradable materials. These known anchors have relied upon mechanical interlocks between the body tissue and the anchor to retain the anchor in place against the influence of forces transmitted through the suture to the anchor. It has previously been suggested to construct anchors in the manner disclosed in U.S. Pat. Nos. 5,405,359; 5,403,348; 5,203,787; 5,046,513; and 5,041,129. In addition, an anchor formed of body tissue is disclosed in co-pending application Ser. No. 08/626,393 filed Mar. 29, 1996 filed by Peter M. Bonutti and entitled "Suture Anchor".

SUMMARY OF THE INVENTION

The present invention relates to a new and improved suture anchor which absorbs body liquid. A suture extends from the anchor. The anchor and the suture are inserted into a patient's body. When the anchor is disposed in the patient's body, the anchor expands. The anchor expands by absorbing body liquid and/or by its own natural resilience. As the anchor expands, an improved interlock is obtained between the anchor and the body tissue to enable the anchor to resist relatively large tension forces transmitted through the suture.

The anchor may be formed of a material which absorbs body liquid. Alternatively, the anchor may contain cells which are expanded to absorb body liquid.

The anchor may have a leading end portion which forms an opening in an imperforate body surface. Alternatively, the anchor may be inserted into body tissue through an opening formed in the body tissue by a member other than the anchor. The configuration of the anchor may be changed while the anchor is in the body tissue.

BRIEF DESCRIPTION OF THE DRAWINGS

The foregoing and other features of the invention will become more apparent upon a consideration of the following description taken in connection with the accompanying drawings, wherein:

FIG. 1 is a schematic illustration depicting the manner in which an anchor is inserted into a patient's body with a suture extending into the anchor;

FIG. 2 is a schematic illustration depicting the manner in which the anchor of FIG. 1 is pivoted in the patient's body;

FIG. 3 is a schematic illustration depicting the manner in which the patient's body tissue is secured with the anchor immediately after the anchor has been inserted into the patient's body;

FIG. 4 is a schematic illustration, generally similar to FIG. 3, illustrating the manner in which the anchor expands by absorbing body liquid after the anchor has been inserted into the patient's body;

FIG. 5 is a schematic illustration depicting another manner in which the anchor of FIG. 1 may be inserted into a patient's body;

FIG. 6 is a schematic illustration depicting the manner in which the anchor of FIG. 5 expands in the patient's body by absorbing body liquid;

DESCRIPTION OF SPECIFIC PREFERRED EMBODIMENTS OF THE INVENTION

General Description

Figure 7:
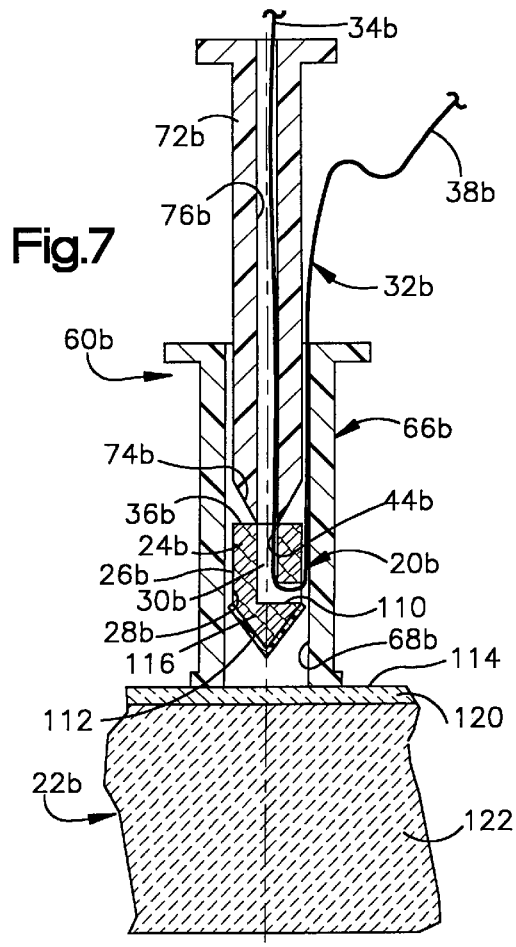
FIG. 7 is a schematic illustration, generally similar to FIG. 1, illustrating the manner in which a second embodiment of the anchor may be inserted into a patient's body through an imperforate surface on body tissue.

Suture anchors have previously been utilized to retain sutures in either hard or soft tissue in a human patient's body. The suture anchors have previously been formed of metal, biodegradable materials, and other materials. These known suture anchors have been retained in the patient's body by changing the orientation of the anchor relative to the patient's body once it has been inserted into the patient's body. Alternatively, known anchors have been retained in the patient's body by a mechanical interlock formed with the material of the patient's body by barbs or other projections.

In accordance with one of the features of the present invention, sutures may be retained in a patient's body by anchors which are at least partially formed of material which absorbs body liquid when exposed to the body liquid. The material expands as it absorbs the liquid in the patient's body. As the anchor expands, an improved interlock is formed between the anchor and body tissue of the patient's body. The improved interlock enables relatively large forces to be transmitted through a suture to the anchor.

In accordance with another of the features of the present invention, sutures may be retained in a patient's body by anchors which are formed of material which expands under the influence of its own natural resilience. As the material expands, cells are expanded from a collapsed condition. As the cells expand, the anchor absorbs body liquid by at least partially filling the cells with body liquid. As the anchor expands, an improved interlock is formed between the anchor and tissue of the patient's body. If desired, the material which forms the cells could also absorb body liquid.

In accordance with another feature of the invention, the anchor could be inserted into a patient's body through an imp erforate surface on body tissue. This may be done by forming an opening in the body tissue with a leading end portion of the anchor. Alternatively, the opening could be formed by one or more members other than the anchor. Once the anchor has entered the patient's body the configuration of the anchor may be changed under the combined influence of force transmitted to the anchor through the suture and force applied against the outer surface of the anchor by body tissue.

Suture Anchor Formed of Material Which Absorbs Body Liquid

A suture anchor 20 (FIG. 1) is formed of a material which absorbs body liquid when t he anchor is exposed to body liquid. As the material of the anchor 20 absorbs body liquid, the anchor expands from the initial volume of FIGS. 1–3 to the expanded volume of FIG. 4. As the material of the anchor 20 absorbs body liquid and expands, the volume of the anchor increases and an improved mechanical interlock is formed between the anchor and body tissue in which the anchor has been inserted. The improved interlock enables the anchor 20 to resist large tension forces in a suture 32 without pulling out of body tissue 22.

It is contemplated that the anchor 20 could be completely formed of material which absorbs body liquid. Alternatively, th e anchor could be partially formed of material which absorbs body liquid and partially formed of material which does not absorb body liquid. The material which does not absorb body liquid may be provided with projections which are forced into the body upon expansion of the material which absorbs body liquid. This would result in at least two different interlocks being obtained between the anchor and the body tissue, that is, a n interlock due to expansion of the material which absorbs body liquid and an interlock due to engagement of projections on the material which does not absorb body liquid with the body tissue.

The suture anchor 20 is entirely formed of material which absorbs body liquid. In one specific instance, the suture anchor 20 was formed of a polymeric material which absorbs body liquid. The polymeric material may be either a copolymer or a dipolymer. The polymeric material may be hydrophilic. The polymeric material may be cellulose, petroylglutamic acid, high purity carboxymethylcellulos e, a collagen, or polylactide. It is believed that a ceramic as found in hydroxyapatite composites with polyethylene, polylactide or polyhydroxybutyrate may be utilized to form the anchor 20. Of course, the suture anchor 20 could be formed of other known materials which absorb body liquid.

It is theorized that the hydrophilic material forming the anchor 20 attracts body liquid under the influence of molecular attraction and establishes molecular linkages with the body liquid. The material forming the anchor 20 is body liquid permeable. The body liquid enters minute cavities in the porous material forming the anchor 20 under the influence of capillary action. The attractive forces between molecules of the body liquid and molecules of the material forming the anchor 20 holds the body liquid in the minute cavities in the material forming the anchor.

In the embodiment of the invention illustrated in FIGS. 1–3, the suture anchor 20 has a tubular cylindrical configuration. The suture anchor 20 has a tubular wall 24 formed of material which absorbs body liquid. The tubular wall 24 has a cylindrical outer side surface 26 which is coaxial with a cylindrical inner side surface 28. The cylindrical inner side surface 28 forms a cylindrical passage 30 which extends axially through the center of the suture anchor 20.

The wall 24 of the suture anchor 20 is formed as one piece of a porous hydrophilic polymer which absorbs body liquid. Although it is preferred to form the anchor 20 with a cylindrical configuration, the anchor may be shaped or ground to any one of many different axially tapering or flaring configurations, such as those disclosed in U.S. Pat. No. 5,403,348. It is believed that it may be preferred to form the anchor 20 with either a cylindrical configuration or a polygonal configuration.

Although it is contemplated that the tubular cylindrical suture anchor 20 could be of many different sizes, it is believed that the suture anchor may preferably have a length or axial extent of between 2 and 4 millimeters. The cylindrical outer side surface 26 of the suture anchor 20 may have a diameter of between 1 and 2 millimeters. The cylindrical inner side surface 28 of the passage 30 in the anchor 20 may have a diameter of ½ to 1 millimeter. Of course, the suture anchor 20 could be formed with many different dimensions and/or shapes if desired.

A suture 32 is inserted into the passage 30 in the suture anchor 20. The suture 32 includes a portion or leg 34 which extends away from a flat annular trailing end surface 36 of the anchor 20. In addition, the suture 32 has a second portion or leg 38 which extends across a flat annular leading end surface 40 of the anchor 20. The leg 38 of the suture 32 extends along the cylindrical outer side surface 26 of the anchor 20 to a location adjacent to and spaced from the leg portion 34 of the suture 32. A relatively short portion 44 of the suture 32 interconnects the leg portions 34 and 38 and is disposed in the passage 30 in the suture anchor 20.

An inserter assembly 60 is used to position the suture anchor 20 and a portion of the suture 32 in a patient's body tissue 22. The inserter assembly 60 includes a cylindrical tubular outer sleeve 66 having a cylindrical central passage 68 in which the anchor 20 is disposed. The inserter 60 also includes a cylindrical tubular inner sleeve 72 which is telescopically received in the outer sleeve 66. The tubular inner sleeve 72 has a conical tapered leading end portion 74 which engages an annular trailing end surface 36 of the anchor 20.

The leg or portion 34 of the suture 32 extends through a cylindrical passage 76 in the inner sleeve 72. The leg or portion 38 of the suture 32 extends through the central passage 68 in the outer sleeve 66 along a path which extends between the inner and outer sleeves. The leg or portion 38 of the suture 32 could extend along the outside of the outer sleeve 66. If desired, one of the legs or portions 34 or 38 of the suture could be omitted. If this was done, the suture 32 could be tied or otherwise secured to the anchor 20.

It is contemplated that the anchor 20 may be inserted into a human patient's body at many different locations. The anchor 20 may be inserted into either hard or soft tissue. In the situation illustrated schematically in FIG. 1, the anchor 20 is being inserted into bone tissue 22 in a patient's body. A cylindrical recess 80 is formed in the bone tissue 22 of the patient's body by drilling or other methods. The recess 80 extends through a hard compact outer layer 82 of the patient's bone tissue 22 into the relatively porous inner or cancellous tissue 84.

To insert the anchor 20 in the patient's body tissue 22, the cylindrical inner sleeve 72 is moved axially downward (as viewed in FIG. 1) to apply force against a relatively small area on the annular trailing end surface 36 of the anchor 20. Once the anchor 20 has been pushed into the recess 80 by axial movement of the inner sleeve 72 relative to the outer sleeve 66, the leg 38 of the suture 32 is tensioned to apply force against an annular leading end surface 40 of the anchor 20. At the same time, the bevelled leading end 74 of the inner sleeve 72 is pressed against the trailing end surface 36 of the anchor.

This results in the application of a counterclockwise (as viewed in FIGS. 1 and 2) torque to the anchor 20. This torque causes the anchor 20 to pivot through the orientation shown in FIG. 2 to the orientation shown in FIG. 3. Once the anchor 20 has been pivoted to the orientation shown in FIG. 3, by tensioning the suture 32 and applying force against the anchor with the leading end portion 74 of the inner sleeve 72, the anchor 20 engages the hard compact outer layer 82 of the patient's bone tissue to hold the anchor in the recess 80. Thus, a solid initial interlock is obtained between the anchor 20 and body tissue 22.

The suture 32 is then tensioned to secure a member, such as body tissue 90, in place. The member or body tissue 90 may be soft tissue, or a ligament, or a tendon, or other body tissue. If desired, the suture 32 may be used to secure other members, such as an implant or splint, in place relative to the patient's body tissue 22. The suture is tensioned to transmit force between the anchor 20 and a member to be held in place.

One specific known inserter assembly 60 and method of inserting a suture anchor 20 into a patient's body tissue has been illustrated in FIGS. 1–3. This specific inserter assembly and the method of inserting the anchor 20 are the same as is disclosed in U.S. Pat. No. 5,403,348 issued Apr. 4, 1995 and entitled "Suture Anchor". However, it is contemplated that many different known types of inserter assemblies could be utilized to install the suture anchor 20 with many different methods in a patient's body tissue. For example, the inserter assembly and method disclosed in U.S. Pat. No. 5,464,426 issued Nov. 7, 1995 and entitled "Method of Closing Discontinuity in Tissue" could be utilized if desired. Of course, other known apparatus and methods could also be utilized if desired.

In accordance with a feature of the invention, the suture anchor 20 absorbs body liquid and expands once the suture anchor has been inserted into the body tissue 22. The expansion of the suture anchor 20 improves the initial interlock between the anchor and body tissue 22. The initial interlock between the anchor 20 and body tissue 22 is obtained by pivoting the anchor in the body tissue to the orientation shown in FIG. 3. The improved interlock is obtained by expanding the anchor 20, as shown in FIG. 4. The improved interlock allows relatively large tension forces to be transmitted through the suture 32 between the anchor 20 and a member to be held in place by the suture.

The suture anchor 20 expands in all directions, from the initial size illustrated in FIG. 3 to a relatively large expanded size illustrated in FIG. 4, shortly after the suture anchor has been inserted into the body tissue 22. After the suture anchor 20 has been inserted into the body tissue 22, the suture anchor is exposed to body liquids, indicated schematically at 98 in FIG. 4. The body liquids 98 are drawn into the suture anchor 20 due to the affinity of the polymeric material forming the suture anchor 20 for body liquids.

As the body liquids 98 are drawn into the suture anchor 20, the anchor expands in a substantially uniform manner in all directions. Thus, the anchor 20 swells both radially and axially. Substantially uniform expansion of the entire outer side surface area of the suture anchor 20 occurs as body liquids 98 are absorbed by the anchor. The extent of expansion of the suture anchor 20 will depend upon the specific characteristics of the material from which the suture anchor is formed and may vary between 10 and 50 percent by volume. Of course, the extent of expansion of the anchor 20 will be a function of the force applied against the outer side surface of the anchor by the body tissue 22.

As the suture anchor 20 swells, the size of the anchor 20 increases. As the size of the anchor 20 increases, the outer side surface of the anchor presses both axially and radially outward against the body tissue 22. As the anchor 20 expands and presses against the body tissue, the body tissue is displaced by the anchor. Thus, the outer side surface of the anchor 20 applies force against the body tissue 22 and moves the body tissue to make room for the anchor as the anchor expands. If the anchor 20 encounters a localized area of high resistance to expansion in the body tissue, the anchor will expand around the localized area and may even shift in the body tissue 22.

The expansion of the anchor 20 as it absorbs the body liquids 98 results in an increasing mechanical interlocking action between the anchor 20 and the body tissue 22. There is an initial mechanical interlock between the anchor 20 and the body tissue 22 when the anchor has its original or initial size (FIG. 3). As body liquids 98 are absorbed by the suture anchor 20 and the volume of the anchor increases, the anchor expands to improve the mechanical interlock between the anchor and the body tissue 22. The improved interlock between the anchor 20 and body tissue 22 allows relatively large tension forces to be transmitted through the suture 32 without pulling the anchor out of the body tissue.

Installation-Second Procedure

In the embodiment of the invention illustrated in FIGS. 1–4, the anchor 20 was pivoted from the orientation shown in FIG. 1 through the orientation shown in FIG. 2 to the orientation shown in FIG. 3 to obtain an initial mechanical interlock between the anchor and body tissue 22. In the embodiment of the invention illustrated in FIGS. 5 and 6, the anchor is not pivoted from its initial orientation to obtain an initial mechanical interlock. The anchor is merely positioned in the body tissue and expanded in all directions by absorbing body liquid. The expansion of the anchor results in the formation of an interlock between the anchor and the body tissue. Since the embodiment of the invention illustrated in FIGS. 5 and 6 is generally similar to the embodiment of the invention illustrated in FIGS. 1–4, similar numerals will be utilized to designate similar components, the suffix letter "a" being associated with the numerals of FIGS. 5 and 6 in order to avoid confusion.

The suture anchor 20a has the same construction and is formed of the same hydrophilic polymeric material as the suture anchor 20 of FIGS. 1–3. The suture anchor 20a (FIG. 5) has a cylindrical tubular configuration. The suture anchor 20a has a cylindrical outer side surface 26a. A cylindrical central passage 30a extends through the suture anchor 20a between opposite annular end surfaces 36a and 40a of the suture anchor 20a.

A suture 32a has a leg 34a which extends through a passage 76a formed in an inner sleeve 72a. A second leg 38a of the suture 32a extends through a central passage 68a and a tubular outer sleeve 66a. The leg 38a of the suture 32a extends between a cylindrical inner side surface 68a of the inner sleeve 72a and a cylindrical inner side surface of the outer sleeve 66a.

It is contemplated that the anchor 20a may be inserted into a patient's body at many different locations. The anchor 20a may be inserted into either hard or soft tissue. In the situation illustrated schematically in FIG. 5, the anchor is being inserted into bone tissue 22a in a patient's body with the inserter assembly 60a. A recess 80a is formed in the bone tissue 20a of the human patient's body by drilling or other methods. The cylindrical recess 80a extends through the hard compact outer layer 82a of the patient's bone tissue 20a into the relatively porous inner or cancellous tissue 84a.

To insert the anchor 20a in the patient's body tissue 22a, the inner sleeve 72a is moved axially downward (as viewed in FIG. 5) to apply force against the trailing end surface 36a of the anchor 20a. In this embodiment of the inserter assembly 60a, the inner sleeve 72a has a cylindrical leading end portion 74a which applies a substantially uniform force over substantially the entire flat annular trailing end surface 36a of the anchor 20a. Therefore, the anchor 20a is not pivoted but is merely moved straight into the recess 80a.

Once the anchor 20a has been positioned in the recess 80a, the anchor absorbs body liquid 98a and increases in volume as the liquid is absorbed. This results in the anchor expanding in all directions from the initial size of FIG. 5 to a relatively large expanded size illustrated in FIG. 6. As the anchor 20a expands, its size increases by 10 to 50 percent by volume.

The anchor 20a is porous and is formed of a hydrophilic material. The body liquid 98a is drawn into openings in the porous material of the anchor 20a by the affinity of the porous material forming the anchor for the body liquid. The attractive forces between the material forming the anchor 20a and the body liquid holds the body liquid in the anchor.

As the anchor 20a expands from the initial size, the outer surfaces on the anchor press radially and axially against the body tissue 22a. Substantially uniform expansion of the anchor 20a forms a secure mechanical interlock with the body tissue. This interlock enables tension forces to be transmitted through the suture 32a between the anchor 20a and a member, such as the body tissue 90a.

As the anchor 20a expands radially outward, the cancellous tissue 84a is compressed and the size of the portion of the recess 80a in the cancellous tissue 84a is increased. As this happens, the diameter of the cylindrical anchor 20a increases from a diameter which is just slightly less than the size of the portion of the recess 80a which extends through the hard compact outer layer 82a of the bone tissue 22a to a diameter which is greater than the diameter of the portion of the recess 80a extending through the hard compact outer layer 82a of bone tissue. This results in the anchor 20a being locked in place in the body tissue 22a.

The suture 32a can then be used to secure a member 90a in place in the manner illustrated schematically in FIG. 6. The member 90a may be soft body tissue, or a ligament, or a tendon, or other body tissue. If desired, the suture 32a may be used to secure an implant or splint in place relative to the patient's body 22a. The interlock between the anchor 20a and body tissue 22a enables substantial tension force to be transmitted through the suture 32a without pulling the anchor out of the body tissue.

The expansion of the anchor 20a has been schematically illustrated in FIG. 6 as being uniform in all directions. This will be the case when the body tissue 22a applies uniform forces against all sides of the anchor 20a. However, the body tissue 22a may provide nonuniform resistance to expansion of the anchor 20a. When this occurs, the anchor 20a may shift in the body tissue 22a under the influence of forces applied against the body tissue as the anchor expands. In addition or alternatively, the anchor 20a may expand in a nonuniform manner.

Anchor—Second Embodiment

In the embodiment of the invention illustrated in FIGS. 1–4, the anchor 20 has a generally cylindrical configuration and is formed entirely of a hydrophilic polymeric material which absorbs body liquid. The anchor illustrated in FIGS. 1–4, due to its relatively blunt leading end portion, is particularly well adapted for positioning in preformed recesses in body tissue. In the embodiment of the anchor illustrated in FIG. 7, the anchor has a sharp or pointed leading end portion to facilitate forming an opening in imperforate body tissue. Since the embodiment of the invention illustrated in FIG. 7 is generally similar to the embodiment of the invention illustrated in FIGS. 1–4, similar numerals will be utilized to designate similar components, the suffix letter "b" being associated with the numerals of FIG. 7 to avoid confusion.

The tubular cylindrical suture anchor 20b has a generally cylindrical outer side surface 26b which is coaxial with a cylindrical inner side surface 28b. The cylindrical inner side surface 28b forms a portion of a passage 30b which extends through the anchor 20b. In addition to the main portion of the passage 30b formed by the cylindrical side surface 28b, a second cylindrical side surface 110 has a central axis which extends perpendicular to the central axis of the cylindrical side surface 28b. The cylindrical side surface 110 intersects the cylindrical side surface 28b and extends radially outward from the cylindrical side surface 28b. The cylindrical side surfaces 28b and 110 cooperate to form the passage 30b with a generally L-shaped configuration.

A suture 32b is inserted into the passage 30b in the suture anchor 20b. The suture 32b includes a portion or leg 34b which extends away from a flat annular trailing end surface 36b of the anchor 20b. In addition, the suture 32b has a second portion or leg 38b which extends along the cylindrical outer side surface 26b of the anchor 20b and along the cylindrical inner side surface 68b of the outer sleeve 66b. A relatively short portion 44b of the suture 32b interconnects the leg portions 34b and 38b and is disposed in the passage 30b in the suture anchor 20b.

An inserter assembly 60b is used to position the suture anchor 20b and a portion of the suture 32b in a patient's body tissue 22b. The inserter assembly 60b includes a generally cylindrical tubular outer sleeve 66b having a central passage 68b in which the anchor 20b is disposed. The inserter 60b also includes a tubular inner sleeve 72b which is telescopically received in the outer sleeve 66b. The tubular inner sleeve 72b has a conical tapered leading end portion 74b which engages the trailing end surface 36b of the anchor 20b.

In accordance with a feature of the embodiment of the invention illustrated in FIG. 7, the anchor 20b has a leading end portion 112 with a generally conical configuration. The leading end portion 112 of the anchor 20b is adapted to form an opening in an imperforate outer side surface 114 of the patient's body tissue 22b. In addition, the leading end portion 112 of the anchor 20b facilitates moving the anchor into the body tissue 22b under the influence of force applied against the trailing end surface 36b of the anchor 20b by the tubular inner sleeve 72b. The conical leading end portion 112 of the anchor 20b is formed by a conical layer of a relatively hard polymeric material. The polymeric material forming the leading end portion 112 may be biodegradable if desired.

In addition, the anchor 20b has a cylindrical body portion or wall 116 which is disposed in a coaxial relationship with the leading end portion 112. The cylindrical body portion 116 is formed of a hydrophilic polymeric material which absorbs body liquid when exposed to the body liquid. The cylindrical body portion 116 is formed of the same material as the anchor 20 of FIGS. 1–4. As the body portion 116 of the anchor 20b absorbs body liquid, the body portion of the anchor expands radially and axially to interlock with the body tissue 22b. The leading end portion 112 is formed of a rigid polymeric material which does not absorb body liquid.

The leading end portion 74b of the tubular inner sleeve 72b is tapered so that it applies force against the trailing end surface 36b of the anchor 20b at a relatively small area on the trailing end surface. The concentrated application of force to the trailing end surface 36b of the anchor 20b facilitates pivoting movement of the anchor in the body tissue 22b upon tensioning of the leg 38b of the suture 32b.

Assuming the anchor 20b is to be moved into body tissue 22b disposed beneath a layer 120 of skin, force is applied against the tubular inner sleeve 72b to force the pointed leading end portion 112 of the anchor against the imperforate outer side surface 114 of the skin 120. This force causes the anchor 20b to pierce the skin 120 and enter soft body tissue 122 disposed beneath the skin. Once the anchor 20b has been moved completely beneath the skin 120 into the soft body tissue 122, the leg 38b of the suture 32b is tensioned. This results in the application of torque to the anchor 20b tending to rotate or pivot the anchor in a counterclockwise direction from the orientation shown in FIG. 7 to a generally horizontal orientation, corresponding to the orientation of the anchor illustrated in FIG. 3. At this time, the longitudinal central axis of the anchor will be generally parallel to the skin 120.

Once the anchor 20b has been moved into the body tissue 122 and pivoted in the manner previously explained, the body portion 116 of the anchor will absorb body liquid, such as blood or other fluids. As the hydrophilic body portion 116 of the anchor 20b absorbs body liquids, the body portion expands in all directions and presses against the body tissue 122. As the anchor expands, body tissue is displaced and the mechanical interlock with the anchor 20b is enhanced.

Thus, the anchor 20b is mechanically interlocked with the body tissue 122 by both pivotal movement of the anchor to a sidewise orientation and expansion of the anchor as it absorbs body liquids. The improved interlock obtained by expanding the anchor 20b enables relatively large tension forces to be transmitted between a member (not shown) and the anchor 20b through the suture 32b.

Anchor—Third Embodiment

Figure 8:
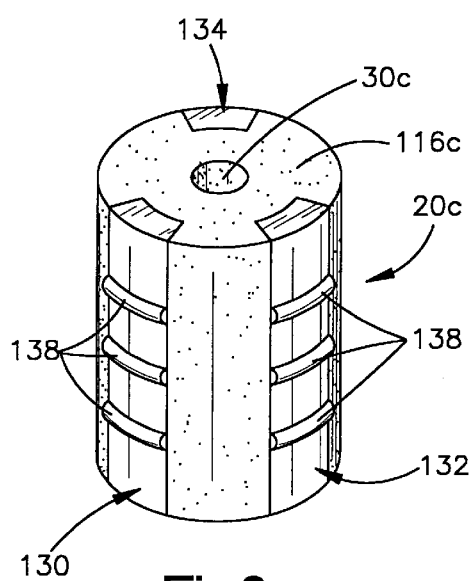
FIG. 8 is a schematic pictorial illustration of a third embodiment of the anchor having a portion which absorbs body liquid and a portion which does not absorb body liquid and has projections to engage body tissue.

In the embodiment of the anchor illustrated in FIGS. 1–4, the anchor is formed entirely of material which absorbs body liquid when it is exposed to the body liquid. In the embodiment of the anchor illustrated in FIG. 8, a portion of the anchor is formed of material which absorbs body liquid and another portion of the anchor is formed of material which does not absorb body liquid. The material which does not absorb body liquid has projections which engage body tissue to enhance an interlock between the anchor and the body tissue. Since the embodiment of the invention illustrated in FIG. 8 is generally similar to the embodiment of the invention illustrated in FIGS. 1–4, similar numerals will be utilized to designate similar components, the suffix letter "c" being associated with the numerals of FIG. 8 in order to avoid confusion.

An anchor 20c (FIG. 8) has a tubular cylindrical configuration. A suture (not shown) extends through a central passage 30c in the anchor 20c in the same manner as illustrated in FIG. 1 for the anchor 20.

In accordance with a feature of this embodiment of the invention, the anchor 20c (FIG. 8) has a body portion 116c which is formed of a hydrophilic polymeric material which absorbs body liquid when exposed to the body liquid. In addition, the anchor 20c includes a plurality of identical retaining portions 130, 132 and 134. The retaining portions 130, 132 and 134 are formed of a relatively hard polymeric material which does not absorb body liquid. The retaining portions 130, 132 and 134 may be biodegradable if desired.

In the illustrated embodiment of the invention, the retaining portions 130, 132 and 134 and a plurality of ribs or projections 138 which extend outward from the retaining portion. When the anchor 20c is positioned in body tissue in the manner previously explained in conjunction with the embodiments of the invention illustrated in FIGS. 1–4, the body portion 116c absorbs body liquid. When this occurs, the body portion 116c of the anchor 20c expands radially and axially outward to enhance the mechanical interlock with the body tissue.

As the body portion 116c of the anchor 20c expands, the retaining portions 130, 132 and 134 are moved radially outward away from the central axis of the anchor 20c. This presses the ribs 138 on the retaining portions 130, 132 and 134 into the body tissue to further enhance the mechanical interlock between the anchor and the body tissue. Although the ribs 138 have been shown in FIG. 8 as having a generally arcuate configuration and a generally smooth outer side surface, it is contemplated that the ribs could have barbs or other projections which would impale the body tissue as the body portion 116c of the anchor 20c absorbs body liquid and expands. Of course, this would further enhance the mechanical interlock between the anchor 20c and the body tissue.

In the embodiment of the anchor 20c illustrated in FIG. 8, the anchor has a generally flat annular leading end portion. However, it is contemplated that the anchor 20c could be provided with a conical leading end portion, similar to the conical leading end portion 112 on the anchor 20b of FIG. 7. If the anchor 20c were to be provided with a conical leading end portion, it is contemplated that the retaining portions 130, 132 and 134 could be extended in an axial direction to form the conical leading end portion as three separate segments. As the body portion 116c of the anchor 20c absorbs body liquid and expands, the retaining portions 130, 132 and 134 would move radially outward away from each other and the leading end portion of the anchor would expand.

A relatively strong interlock is obtained between the anchor 20c and body tissue. This interlock is obtained by changing the orientation of the anchor 20c relative to the body tissue, in the manner illustrated for the anchor 20 in FIG. 2. In addition, the interlock is obtained by expansion of the anchor 20c as the body portion 116c absorbs body liquid. The interlock is also obtained by engagement of the ribs 138 with body tissue. The result is a strong interlock which enables the anchor 20c to resist very large tension forces transmitted to the anchor through a suture.

Anchor—Fourth Embodiment

Figure 9:
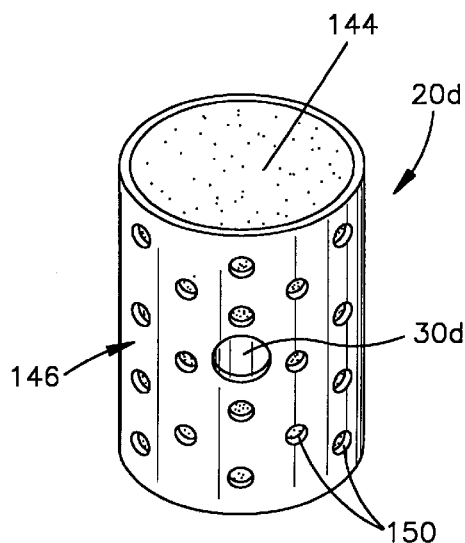
FIG. 9 is a schematic pictorial illustration of a fourth embodiment of the anchor having a core which absorbs body liquid and a casing formed of an elastic material which does not absorb body liquid.

In the embodiment of the anchor 20 illustrated in FIGS. 1–4, the anchor is formed entirely of material which expands when it is exposed to body liquid. In the embodiment of the invention illustrated in FIG. 9, the anchor is formed by a core of material which expands upon being exposed to body liquid and an elastic jacket which encloses the core. Since the embodiment of the invention illustrated in FIG. 9 is generally similar to the embodiment of the invention illustrated in FIGS. 1–4, similar numerals will be utilized to designate similar components, the suffix letter "d" being associated with the numerals of FIG. 9 in order to avoid confusion.

An anchor 20d (FIG. 9) has a cylindrical configuration. The anchor 20d includes a cylindrical core 144 which is enclosed by a tubular cylindrical jacket 146. A passage 30d extends through both the core 144 and the jacket 146. The passage 30d extends diametrically through the core 144 and the jacket 146 and has a cylindrical configuration. A suture (not shown) is positioned in the passage 30d. The suture may be tied off at one end of the passage or may extend through the passage so that legs of the suture extend along opposite sides of the jacket 146.

The jacket 146 is provided with a plurality of circular openings 150 which extend through the jacket. The openings 150 enable body liquid to pass through the jacket into the core 144. The jacket 146 is formed of an elastic polymeric material which is easily stretched. The core 144 is formed of a material which absorbs body liquid upon being exposed to the body liquid. In one specific embodiment of the suture anchor 20d, the core 144 was formed of a hydrophilic polymeric material which is the same as the material forming the anchor 20 of FIGS. 1–4.

When the anchor 20d is inserted into body tissue, in the manner illustrated schematically in either FIGS. 1–3 or 5 and 6, the entire anchor 20d is exposed to body liquid. The body liquid passes through the openings 150 and is absorbed by the core 144. As the core 144 absorbs body liquid, the core expands and stretches the jacket 146.

Although the anchor 20d has been shown as having a generally cylindrical configuration with flat annular end surfaces, it is contemplated that the anchor could be provided with a conical leading end portion, similar to the conical leading end portion 112 of the anchor 20b of FIG. 7. The conical leading end portion could be formed either as a portion of the jacket 46 or separately from the jacket. It is believed that it may be preferred to form a conical leading end portion for the anchor 20d separately from the jacket 146 to enable the leading end portion to be formed of a hard material which is not readily stretched and which is capable of piercing an imperforate surface of body tissue.

In the illustrated embodiment of the invention, the jacket 146 is formed of a material which is resiliently stretched when the core 144 absorbs body liquid and expands. It is contemplated that the size of the jacket 146 could be increased in other ways to accommodate expansion of the core. For example, releasable tucks could be formed in the jacket. Upon expansion of the core, stitches or other devices holding the tucks would be released under the influence of force applied against the jacket by the core.

Anchor—Fifth Embodiment

The anchors illustrated in FIGS. 1–9 all have passages through which the suture extends. In the embodiment of the invention illustrated in FIG. 10, the anchor has an eyelet through which the suture extends. Since the embodiment of the invention illustrated in FIG. 10 is generally similar to the embodiment of the invention illustrated in FIGS. 1–9, similar numerals will be utilized to designate similar components, the suffix letter "e" being associated with the embodiment of the invention illustrated in FIG. 10 to avoid confusion.

An anchor 20e has a solid cylindrical body portion 116e. The body portion 116e of the anchor 20e is formed of a hydrophilic polymeric material which absorbs body liquid when exposed to the body liquid. The material forming the body portion of the anchor 20e is the same as the material forming the anchor 20 of FIGS. 1–4. Upon absorbing body liquid, a portion 116e of the anchor 20e expands.

Figure 10:
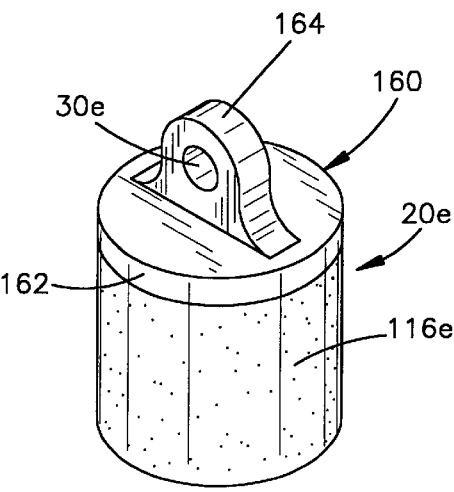
FIG. 10 is a pictorial schematic illustration of a fifth embodiment of the anchor having an end portion with a suture receiving opening formed in material which does not absorb body liquid and is connected with a main portion which absorbs body liquid.

In accordance with a feature of the embodiment of the invention illustrated in FIG. 10, the anchor 20e is provided with a trailing end portion 160 which is connected with a suture. The trailing end portion 160 of the anchor 20e has a circular wall 162 which is fixedly connected with the body portion 116e of the anchor 20e. A passage 30e is formed in a projection 164 which extends axially outward from the end wall 162. The passage 30e receives a suture. The suture may be tied off on the projection 164 or may extend through the projection and have a pair of legs, corresponding to the legs 34 and 38 of the suture 32 of FIG. 1.

When the anchor 20e is inserted into body tissue, using an inserter assembly similar to the inserter assembly 60 of FIGS. 1 and 2, the body portion 116e is exposed to body liquid. This results in the body portion 116e of the anchor 20e expanding radially and axially outward from the trailing end portion 160 to form a mechanical interlock with the body tissue.

Anchor—Sixth Embodiment

Figure 11:
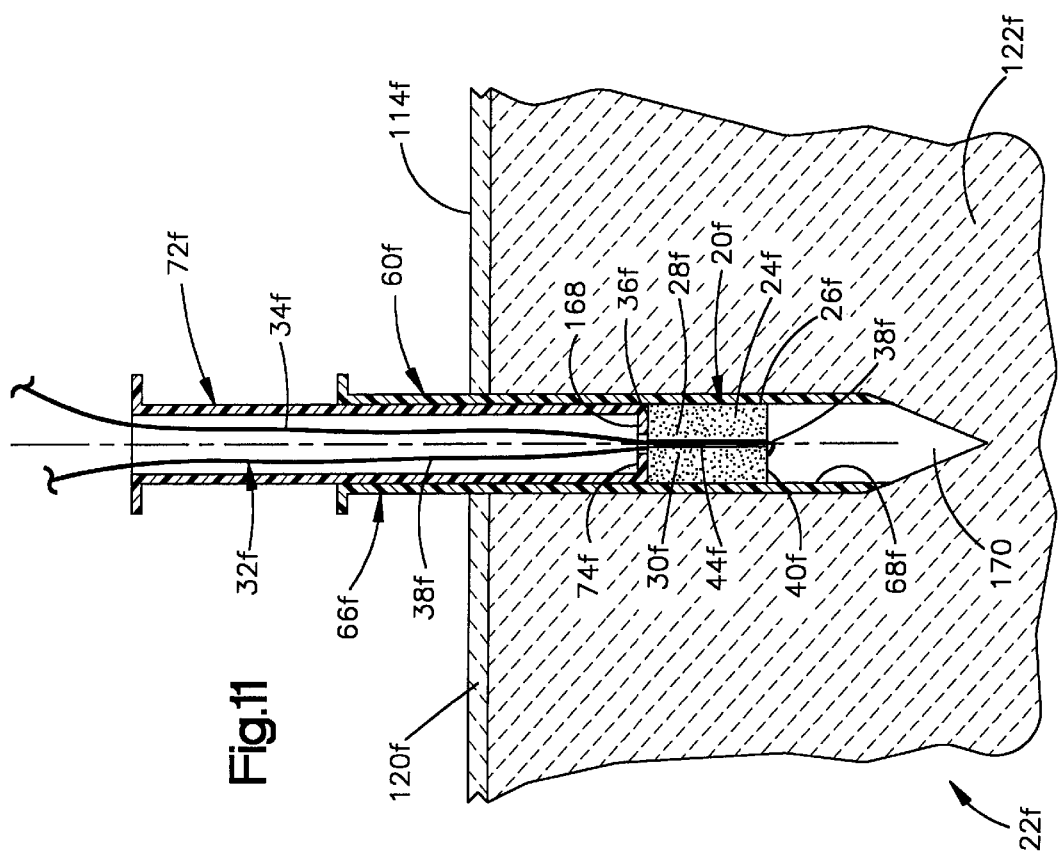
FIG. 11 is a schematic illustration of a an apparatus for inserting an anchor having cells which are collapsed before the anchor is moved into a patient's body.

In the embodiments of the invention illustrated in FIGS. 1–10, at least portions of the anchors are formed of a hydrophilic polymeric material which absorbs body liquid. In the embodiment of the invention illustrated in FIG. 11, the anchor is formed of cellular material which absorbs body liquid. Since the embodiment of the invention illustrated in FIG. 11 is generally similar to the embodiments of the invention illustrated in FIGS. 1–10, similar numerals will be utilized to designate similar components, the suffix letter "f" being associated with the numerals of FIG. 11 to avoid confusion.

A suture anchor 20f has a tubular cylindrical configuration when the anchor is in an unrestrained condition. When the suture anchor 20f is in an unrestrained condition, the anchor has a tubular wall 24f which has a cylindrical outer side surface 26f which is coaxial with a cylindrical inner side surface 28f of the anchor. The cylindrical inner side surface 28f forms a passage 30f which extends axially through the center of the suture anchor 20f when the anchor is in an unrestrained condition.

The wall 24f of the suture anchor 20f is formed as one piece of resilient material containing a large number of cells which are expandable to absorb body liquid. The cellular material which forms the suture anchor 20f may be a hydrophilic polymeric cellular material which absorbs body liquid. Although it is preferred to form the anchor 20f with a cylindrical configuration, the anchor may be shaped to any one of many different axially tapering or flaring configurations or may have a polygonal configuration.

A suture 32f is inserted into the passage 30f in the suture anchor 20f. The suture 32f includes a leg portion 34f which extends away from a flat annular trailing end surface 36f of the anchor 20f. In addition, the suture 32f has a second portion or leg 38f which extends across a flat annular leading end surface 40f of the anchor 20f. The leg 38f of the suture 32f extends along the cylindrical outer side surface 26f. A relatively short portion 44f of the suture 32f interconnects the leg portion 34f and 38f and is disposed in the passage 30f in the anchor 20f.

An inserter assembly 60f is used to position the anchor 20f and a portion of the suture 32f in a patient's body tissue 22f. The inserter assembly 60f includes a cylindrical tubular outer sleeve 66f having a cylindrical passage 68f in which the anchor 20f is disposed. The inserter 60f also includes a cylindrical tubular inner sleeve 72f which is telescopically received in the outer sleeve 66f. The tubular inner sleeve 72f has a cylindrical leading end portion 74f which engages the trailing end surface 36f of the anchor 20f.

The leading end portion 74f of the tubular inner sleeve 72f has an end wall 168 with a flat end surface which abuttingly engages the flat annular trailing end surface 36f on the anchor 20f. The two legs 34f and 36f of the suture 32f extend through a central opening formed in the end wall 168 at the leading end portion 74f of the inner sleeve 72f. The legs 34f and 38f of the suture 32f extend through the tubular inner sleeve 72f to a location remote from the inserter assembly 60f. If desired, one of the legs 34f or 38f of the suture could be omitted. If this was done, the suture 32f could be tied or otherwise secured to the anchor 20f.

It is contemplated that the anchor 20f may be inserted into a human patient's body at many different locations. The anchor 20f may be inserted into either hard or soft tissue. In the situation illustrated schematically in FIG. 11, the anchor 20f is being inserted into soft body tissue in a patient's body.

To facilitate insertion of the anchor 20f into soft body tissue, a leading end portion 170 of the outer sleeve 60f has an axially tapered or pointed configuration. The pointed configuration of the leading end portion 170 of the outer sleeve 60f enables the leading end portion of the outer sleeve to form an opening in an imperforate outer side surface 114f of the patient's body tissue 22f. In addition, the pointed leading end portion 170 of the outer sleeve 60f facilitates moving the outer sleeve 60f into the body tissue 22f under the influence of force manually applied against an outer end portion of the outer sleeve 60f.

To insert the anchor 20f into the patient's body tissue 22f, the pointed leading end portion 170 of the outer sleeve 66f is pressed against the imperforate outer side surface 114f of skin or other tissue 120f. The pointed leading end portion of the outer sleeve 66f pierces the imperforate outer surface 114f of the skin 120f and enters soft body tissue 122f disposed beneath the skin. The outer sleeve 66f is forced into the soft body tissue 22f for a desired distance corresponding to the distance which the suture anchor 20f is to be inserted into the body tissue.

The inner sleeve 72f is then pressed downward (as viewed in FIG. 11) to move the suture anchor 20f to the leading end portion 170 of the outer tubular member 66f. The inner side surface 68f of the tubular outer member 66f applies force against the outer side surface 26f of the anchor 20f to maintain the anchor in the compressed condition shown in FIG. 11. The outer tubular member 66f is then moved axially upward (as viewed in FIG. 11) relative to the stationary inner tubular member 72f. This results in the anchor 20f being ejected from the outer tubular member 66f into the body tissue 22f. Once the anchor 20f has moved from the outer sleeve 66f into the body tissue 22f, both the inner and outer sleeves 66f and 72f are withdrawn from the body tissue.

If desired, a pointed member, such as a trocar, could be inserted through the outer sleeve 66f to pierce the surface 114f and body tissue 22f. If this was done, the inner sleeve 72f and anchor 20f would be removed from the outer sleeve 66f to provide room for the pointed member. After the body tissue has been pierced by the pointed member, the pointed member would be withdrawn from the outer sleeve 66f and the inner sleeve 72f and compressed anchor 20f inserted into the outer sleeve.

In accordance with a feature of the present invention, the anchor 20f is formed of a resilient cellular material. Prior to insertion of the anchor 20f into the outer sleeve 66f, the cellular material of the anchor 20f is resiliently compressed from a relatively large unrestrained size to a compacted size illustrated in FIG. 11. The unrestrained size of the suture anchor 20f may be 2 to 20 times as large as the size illustrated in FIG. 11.

As the resilient cellular material of the anchor 20f is compressed, the passage 30f which extends through the anchor 20f when the anchor is in its unrestrained condition, is collapsed tightly inward against the portion 44f of the suture 32f. In addition, as the anchor 20f is resiliently compressed from its unrestrained condition, the cells in the anchor are collapsed. Thus, the anchor 20f is resiliently compressed from an unrestrained condition to the compacted or compressed condition of FIG. 11 in much the same manner as in which a sponge may be compressed.

The compressed anchor 20f, with the suture 32f extending through the anchor and the inner sleeve 72f, is inserted into the outer sleeve 66f. The inner sleeve 72f then pushes the compressed anchor axially downward (as viewed in FIG. 11) into the outer sleeve as the telescopic relationship between the inner and outer sleeves is increased.

When the anchor 20f is in the outer sleeve 66f, the inner side surface 68f of the outer sleeve applies force against the outer side surface 26f of the anchor to hold the anchor in its compressed condition. Upon movement of the anchor 20f out of the outer sleeve 66f into the body tissue 22f, the force holding the anchor 20f in a compressed condition is removed from the outer side surface 26f of the anchor. As this occurs, the natural resilience of the cellular material forming the anchor 20f causes the anchor to expand.

As the anchor 20f expands, the anchor applies force against the soft body tissue 122f and increases the size of the cavity which was originally formed by the outer sleeve 66f of the inserter assembly 60f. As the anchor 20f expands, it applies force against the soft body tissue 122f and displaces the soft body tissue. Thus, the outer side surface 26f of the anchor 20f is pressed against the soft body tissue 122f and moves the soft body tissue as the anchor expands radially outward.

As the anchor 20f expands, the cells in the anchor are expanded from a collapsed condition to an expanded condition. As the size of the cells in the anchor 20f increases, body liquids are drawn into the cells. Thus, the anchor 20f absorbs body liquid as it expands.

The anchor 20f is formed of a resilient polymeric material having an open cell, sponge-like construction. When the anchor 20f is in the compressed condition illustrated in FIG. 11, the cells are collapsed. As the anchor 20f expands in the body tissue 22f, the cells expand. Since the anchor 20f has an open cellular construction, body liquid can flow into the cells as the anchor expands.

Once the anchor 20f has expanded in the body tissue 22f, the expanded anchor is substantially larger than the opening which was formed in the body tissue by insertion of the outer sleeve 66f into the body tissue. However, it should be understood that due to force applied against the anchor 20f by the body tissue 22f, the anchor may not expand fully back to its unrestrained size. As the outer sleeve 66f is withdrawn from the body tissue, the viscoelastic nature of the body tissue causes the body tissue to come together and close off the passage which was formed by the insertion of the outer sleeve 66f into the body tissue. Thus, the body tissue will move inward and grip the legs or portions 34f and 38f of the suture 32f. The anchor 20f will fill a cavity formed in the body tissue 22f by expansion of the anchor.

The expansion of the anchor 20f in the body tissue results in the formation of an interlock between the anchor and the body tissue to prevent the anchor from being pulled out of the body tissue under the influence of tension applied to the suture 32f. The suture 32f may be used to position a member which is body tissue, in the manner similar to that illustrated in FIGS. 3 and 4, or may be used to position a splint or implant member relative to the body tissue. Since the expanded anchor 20f has a firm interlock with the body tissue 122f, tension forces transmitted through the suture 32f between the anchor 20f and a member held in place by the suture will not pull the anchor 20f out of the body tissue.

In FIG. 11, the compressed suture anchor 20f is being inserted into a solid mass of soft body tissue 122f. However, it is contemplated that the suture anchor 20f could be inserted into either a natural or artificial body cavity. If this was done the suture anchor 20f would expand to at least partially fill the body cavity.

Alternative Anchor Insertion Apparatus

Figure 12:
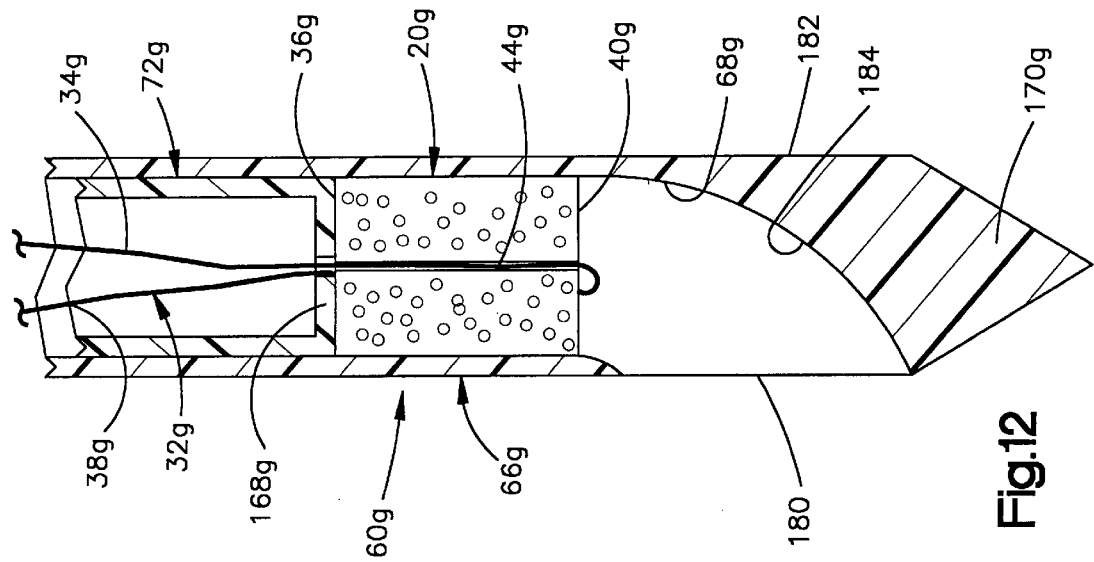
FIG. 12 is a schematic illustration of another apparatus for inserting the anchor of FIG. 11 into body tissue.

In the embodiment of the invention illustrated in FIG. 11, the anchor 20f moves through the open end portion 170 of the outer sleeve 66f into the body tissue 22f. In the embodiment of the invention illustrated in FIG. 12, the outer sleeve has a closed pointed end portion and the anchor is moved from the outer sleeve at a location immediately behind the pointed end portion of the outer sleeve. Since the embodiment of the invention illustrated in FIG. 12 is generally similar to the embodiment of the invention illustrated in FIG. 11, similar numerals will be utilized to designate similar components, the suffix letter "g" being associated with the numerals of FIG. 12 to avoid confusion.

An anchor 20g has the same construction and is formed of the same resilient open cell material as the anchor 20f of FIG. 11. A suture 32g has a leg or portion 34g which extends from a flat annular trailing end surface 36g of the cylindrical anchor 20g. A second leg or portion 38g of the suture 32g extends from a flat annular leading end surface 40g of the anchor 20g. A portion 44g of the suture 32g extends through the anchor and interconnects the legs or portions 34g and 38g.

The two legs or portions 34g and 38g of the suture 32g extend through a cylindrical central passage in an outer sleeve 72g of an inserter assembly 60g. The inner sleeve 72g is disposed in a telescopic relationship with a cylindrical outer sleeve 66g of the inserter assembly 60g. The inner sleeve 72g cooperates with the outer sleeve 66g in the same manner as previously explained in conjunction with the inserter assembly of FIG. 11.

In accordance with a feature of this embodiment of the invention, the outer sleeve 66g has a solid pointed end portion 170g with a generally conical configuration. The pointed end portion 170g is utilized to pierce an imperforate surface of body tissue in much the same manner as in which the end portion 170 of the outer sleeve 66f of the inserter assembly 60f (FIG. 11) is used to pierce an imperforate surface 114f of the body tissue 22f.

In accordance with one of the features of the present invention, the outer sleeve 66g has a generally oval opening 180 in a cylindrical outer side surface 182 of the outer sleeve 66g. The opening 180 is connected with a central passage 68g. The passage 68g extends from an open upper (as viewed in FIG. 12) end portion of the outer sleeve 66g to the solid pointed leading end portion 170g.

When the outer sleeve 66g has been inserted to the desired depth in body tissue, the inner sleeve 72g is moved axially downward (as viewed in FIG. 12) and the anchor 20g is forced along an arcuate cam surface 184 leading to the opening 180. This results in the anchor 20g being forced from the passage 68g in the outer sleeve 66g into the soft body tissue. As this occurs, the leading end 40g of the anchor 20g applies force against the body tissue to displace the body tissue and provide space for the anchor.

As the anchor 20g moves along the passage 68g and through the opening 180, the orientation of the anchor relative to the body tissue changes. Thus, the orientation of the anchor 20g changes from the orientation shown in FIG. 12 to an orientation similar to the orientation of the anchor 20 in FIG. 3. This pivotal movement of the anchor 20g results in the anchor moving from an initial orientation in which a central axis of the anchor extends parallel to and is coincident with a central axis of the outer sleeve 66g to an orientation in which the central axis of the anchor 20g extends perpendicular to the central axis of the outer sleeve 66g.

As the anchor 20g exits from the passage 68g in the outer sleeve 66g. the anchor 20g expands under the influence of its own natural resilience and further displaces body tissue. Once the inner sleeve 72g has been moved downward to the maximum extent possible, that is, to a position in which the leading end of the inner sleeve 72g engages the cam surface 184, the inner and outer sleeves are withdrawn together from the body tissue. As this occurs, engagement of the anchor 20g with the body tissue causes the trailing end portion of the anchor to move out of the passage 68g in the outer sleeve 66g.

As the outer sleeve 66g continues to be withdrawn, the pointed leading portion 170 of the outer sleeve moves upward (as viewed in FIG. 12), past the anchor 20g. As this occurs, the anchor 20g expands into the space previously occupied by the leading end portion 170g of the outer sleeve 66g. As the outer sleeve 66g and inner sleeve 72g are withdrawn from the body tissue, the visco-elastic body tissue closes around the anchor 20g and the legs 34g and 38g of the suture 32g.

As the anchor 20g is forced from the outer sleeve 66g into the body tissue and expands, cells in the anchor 20g also expand. As the cells in the anchor 20g expand, body liquid is drawn into and at least partially fills the cells in the anchor. The anchor 20g has an open cellular construction, similar to the construction of a sponge. The anchor 20g is resiliently compressed prior to insertion into the outer sleeve 66g so that the cells in the anchor 20g are resiliently collapsed until the anchor is allowed to expand as it is forced out of the side opening 180 in the outer sleeve 66g.

Changing Configuration of Anchor

Figure 13:
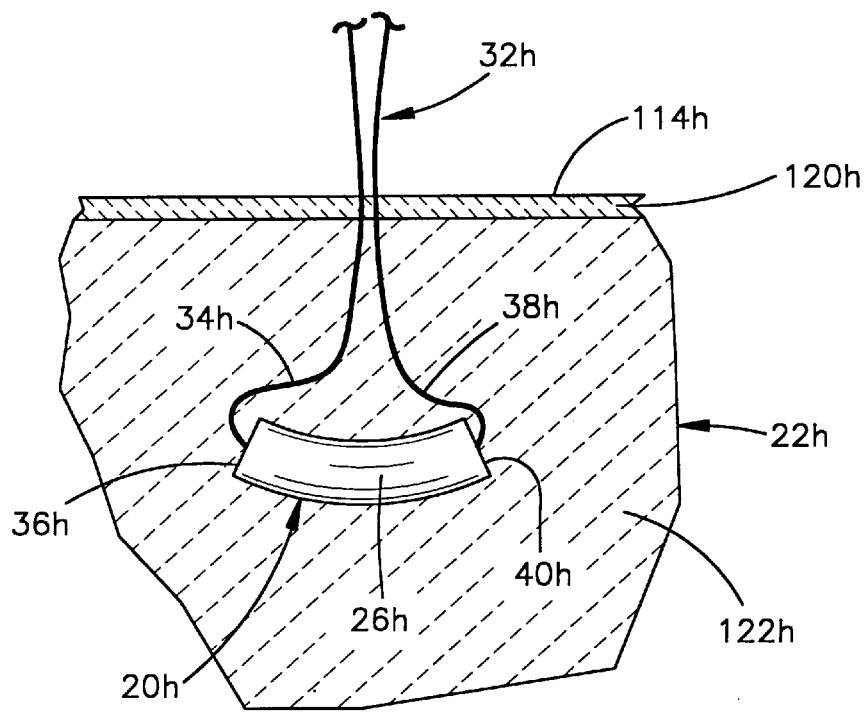
FIG. 13 is a schematic illustration of the manner in which the configuration of an anchor is changed while the anchor is in the patient's body tissue.

In the embodiment of the invention illustrated in FIGS. 1–3, the general configuration of the anchor 20 is illustrated as being maintained constant. Thus, the anchor 20 has a cylindrical tubular configuration with a linear central axis. In the embodiment of the invention illustrated in FIG. 13, the configuration of the anchor is changed while the anchor is in a patient's body tissue. Since the embodiment of the invention illustrated in FIG. 13 is generally similar to the embodiment of the invention illustrated in FIGS. 1–4, similar numerals will be utilized to designate similar components, the suffix letter "h" being associated with the numerals of FIG. 13 to avoid confusion.

A suture anchor 20h has the same construction and is formed of the same hydrophilic polymeric material as the suture anchor 20 of FIGS. 1–3. The suture anchor 20h (FIG. 13) has a cylindrical tubular configuration. The suture anchor 20h has a cylindrical outer side surface 26h. A cylindrical central passage (not shown) extends through the suture anchor 20h between opposite annular end surfaces 36h and 40h of the suture anchor 20h.

A suture 32h has a leg 34h which extends from an annular end surface 36h of the anchor 20h. A second leg 38h of the suture 32h extends from the opposite end surface 40h of the anchor 20h. The anchor 20h is inserted into body tissue 20h in the same manner as in which the anchor 20f of FIG. 11 is inserted into the body tissue 22f. Thus, an inserter assembly, similar to the inserter assembly 60f of FIG. 11, is used to position the anchor 20h in the body tissue 22h. The inserter assembly may include a tubular outer sleeve, corresponding to the sleeve 66f of FIG. 11 and a tubular inner sleeve, corresponding to the inner sleeve 72f of FIG. 11. However, the inner sleeve 72f is provided with a conical leading end portion having a configuration corresponding to the configuration of the leading end portion 74 (FIG. 1) of the inner sleeve 72. This enables the inserter assembly to pivot the suture anchor 20h to the position shown in FIG. 13.

The outer sleeve of the inserter assembly which is used to position the anchor 20h in the body tissue 22h has a pointed leading end portion, corresponding to the pointed leading end 170 of the outer sleeve 66f of the inserter assembly 60f of FIG. 11. The pointed leading end of the outer sleeve of the inserter assembly was used to pierce the imperforate outer side surface 114h of skin 120h and to enter soft body tissue 122h.

As the anchor 20h was positioned in the soft body tissue 122h, the opposite legs 34h and 38h of the suture 32h were tensioned. This resulted in the suture 32h applying force against the opposite flat annular end surfaces 36h and 40h of the anchor 20h. The force applied to opposite ends of the anchor 20h by the suture 32h pulled the outer side surface 26h of the anchor against the body tissue 122h. In addition, the force applied against opposite ends of the anchor 20h by the suture 32h caused the suture to bend from an initial configuration to the deflected configuration shown in FIG. 13.

When the anchor 20h was in the initial configuration, the anchor 20h had a straight longitudinal central axis, the same as the anchor 20 of FIGS. 1–3. However, tensioning the suture 32h caused the legs 34h and 38h of the suture to apply force against opposite ends of the anchor 20h and pull the anchor against the body tissue 122h. As this occurred, the anchor was deflected to the arcuate configuration illustrated in FIG. 13. Since the anchor 20h is formed of the same hydrophilic polymeric material as the anchor 20 of FIGS. 1–3, the anchor 20h absorbs body fluid and expands in the body tissue 122h while the anchor has the deflected configuration illustrated in FIG. 13.

Deflection of Anchor—Second embodiment

Figure 14:
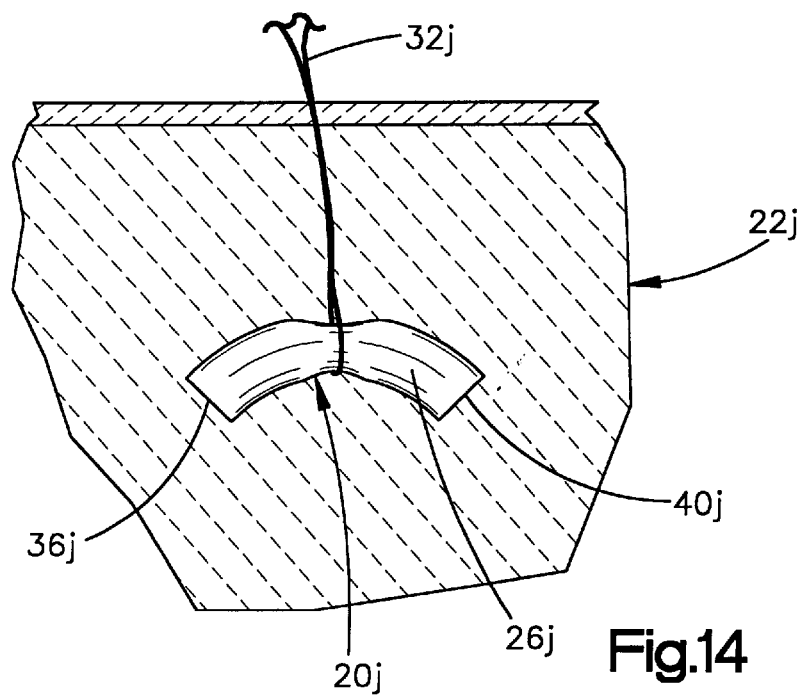
FIG. 14 is a schematic illustration of another manner in which the configuration of an anchor is changed while the anchor is in a patient's body tissue.

In the embodiment of the invention illustrated in FIG. 13, the configuration of the anchor 20h is changed from an initial configuration in which the anchor has a straight longitudinal central axis to a configuration in which the anchor has an arcuate longitudinal central axis by tensioning the suture 32h to apply force against opposite ends of the anchor. In the embodiment of the invention illustrated in FIG. 14, the configuration of the anchor is changed from an initial configuration to a deflected configuration by tensioning a suture which is connected with a central portion of the anchor. Since the embodiment of the invention illustrated in FIG. 14 is generally similar to the embodiment of the invention illustrated in FIG. 13, similar numerals will be utilized to designate similar components, the suffix letter "j" being associated with the numerals of FIG. 14 to avoid confusion.

An anchor 20j has an outer side surface 26j. The outer side surface 26j extends between opposite end surfaces 36j and 40j of the anchor.

A suture 32j is connected with a central portion of the anchor 20j disposed between the opposite end surfaces 36j and 40j. The anchor 20j is formed of the same hydrophilic polymeric material as the anchor 20 of FIGS. 1–3. The anchor 20j is inserted into body tissue 22j in the same manner as described in connection with the embodiment of the invention illustrated FIG. 13.

Prior to insertion of the anchor 20j into the body tissue 22j, the anchor 20j has a solid cylindrical configuration with a straight longitudinal central axis. As the anchor 20j is inserted into the body tissue 22j and moved to the orientation shown in FIG. 14, the suture 32j is tensioned. Tensioning of the suture 32j presses the outer side surface 26j of the anchor 20j against the body tissue 22j. As this occurs, the anchor 20j is deflected from its initial configuration to the deflected configuration illustrated in FIG. 14. When the anchor 20j is in the deflected orientation, the longitudinal central axis of the anchor has an arcuate configuration.

Having described the invention, the following is claimed:

1. A method of anchoring a suture, said method comprising the steps of providing an anchor which is formed of body tissue and which has a suture extending from the anchor, inserting the anchor into a patient's body tissue, said step of inserting the anchor into a patient's body tissue includes moving the anchor into the patient's body tissue with an axis of the anchor extending along the path of movement of the anchor into the patient's body tissue and changing the orientation of the anchor while the anchor is in the patient's body tissue to an orientation in which the axis of the anchor extends transverse to the path of movement of the anchor into the patient's body tissue, and absorbing liquid from the patient's body into the material of the anchor after having performed said step of inserting the anchor into the patient's body tissue.

2. A method as set forth in claim 1 wherein the anchor is formed of collagen which expands as liquid from the patient's body is absorbed into the anchor.

3. A method as set forth in claim 1 wherein said step of changing the orientation of the anchor while the anchor is in the patient's body tissue to an orientation in which the axis of the anchor extends transverse to the path of movement of the anchor into the patient's body tissue includes tensioning the suture and transmitting force from the suture to the anchor at a location offset from a center of the anchor.

4. A method as set forth in claim 1 wherein said step of changing the orientation of the anchor while the anchor is in the patient's body tissue to an orientation in which the axis of the anchor extends transverse to the path of movement of the anchor into the patient's body tissue includes applying force against a trailing end of the anchor.

5. A method as set forth in claim 1 wherein said step of inserting the anchor into a patient's body tissue includes piercing the patient's body tissue with a member while the anchor is in engagement with the member and effecting relative movement between the anchor and member to at least partially separate the anchor and member.

6. A method as set forth in claim 1 further including the step of transmitting force through the suture to secure a member in place under the influence of force transmitted between the anchor and member.

7. A method as set forth in claim 1 wherein said step of inserting the anchor into a patient's body tissue includes piercing the patient's body tissue with a leading end portion of the anchor.

8. A method as set forth in claim 1 wherein said step of inserting the anchor into a patient's body tissue includes moving the anchor through an opening in a hard outer layer of a bone in a patient's body into cancellous tissue enclosed by the hard outer layer of the bone, said step of changing the orientation of the anchor being performed while the anchor is in engagement with the cancellous tissue enclosed by the hard outer layer of the bone.

9. A method as set forth in claim 8 wherein said step of changing the orientation of the anchor includes applying torque to the anchor while the anchor is in engagement with the cancellous tissue enclosed by the hard outer layer of the bone.

10. A method as set forth in claim 1 wherein said step of inserting the anchor into a patient's body tissue includes moving the anchor through an opening in a hard outer layer of a bone into cancellous tissue enclosed by the hard outer layer of the bone, said step of absorbing liquid from the patient's body into the material of the anchor is at least partially performed with the anchor in engagement with the cancellous tissue enclosed by the hard outer layer of the bone.

11. A method as set forth in claim 10 wherein said step of absorbing liquid from the patient's body into the material of the anchor includes increasing the size of the anchor from a first size to a second size, the anchor being movable through the opening in the hard outer layer of bone when the anchor has the first size, the anchor being too large to move through the opening in the hard outer layer of bone when the anchor has the second size.

12. A method as set forth in claim 1 further including the step of changing the configuration of the anchor and a longitudinal central axis of the anchor while the anchor is disposed in the patient's body tissue.

* * * * *